United States Patent [19]

Roscher et al.

[11] 4,353,783

[45] Oct. 12, 1982

[54] PROCESS FOR SEPARATING WATER FROM MIXTURES THEREOF WITH VINYL ACETATE AND ACETIC ACID

[75] Inventors: Günter Roscher, Kelkheim; Karl-Heinz Schmidt, Idstein; Horst Langner, Hattersheim am Main; Hermann Neu, Neu-Isenburg; Aladar Lienerth, Kelkheim; Dominik Dempf, Mehring-Öd; Klaus Kaiser, Burghausen, all of Fed. Rep. of Germany

[73] Assignee: Hoechst Aktiengesellschaft, Frankfurt am Main, Fed. Rep. of Germany

[21] Appl. No.: 201,752

[22] Filed: Oct. 29, 1980

[30] Foreign Application Priority Data

Oct. 31, 1979 [DE] Fed. Rep. of Germany ....... 2943985

[51] Int. Cl.$^3$ .............................................. B01D 3/36
[52] U.S. Cl. ......................................... 203/14; 203/51
[58] Field of Search ................... 560/1, 129, 231, 232, 560/233, 248; 203/12, 14, 16, DIG. 10, 51, 61, 95, 96; 55/29

[56] References Cited

U.S. PATENT DOCUMENTS

| | | | |
|---|---|---|---|
| 3,431,181 | 3/1969 | Bounidt | 560/248 |
| 3,636,087 | 1/1972 | Caserio | 560/248 |
| 4,156,632 | 5/1979 | Roscher et al. | |
| 4,229,261 | 10/1980 | Heck et al. | |

Primary Examiner—Frank Sever
Attorney, Agent, or Firm—Curtis, Morris & Safford

[57] ABSTRACT

Process for separating water from a gas mixture, obtained in the manufacture of vinyl acetate by reacting ethylene with acetic acid and oxygen in contact with catalysts containing palladium or palladium compounds in the gaseous phase said gas mixture consisting essentially of acetic acid, vinyl acetate, water, carbon dioxide and ethylene, wherein (a) the gas mixture leaving the reaction zone is condensed to give a condensate containing the major portion of acetic acid, vinyl acetate and water and (b) an acetic acid solution containing the residual amount of vinyl acetate and water being prepared by absorption of the non-condensed gas in acetic acid, is characterized in that (c) the condensate obtained in step (a) and the solution obtained in step (b) are introduced separately from each other into the same distillation column, the feeding point of the condensate being above the feeding point of the solution, the water is distilled off at the head of said column as azeotrope together with the vinyl acetate and (d) the water phase is removed from the distillate separating into a water phase and a vinyl acetate phase.

2 Claims, 1 Drawing Figure

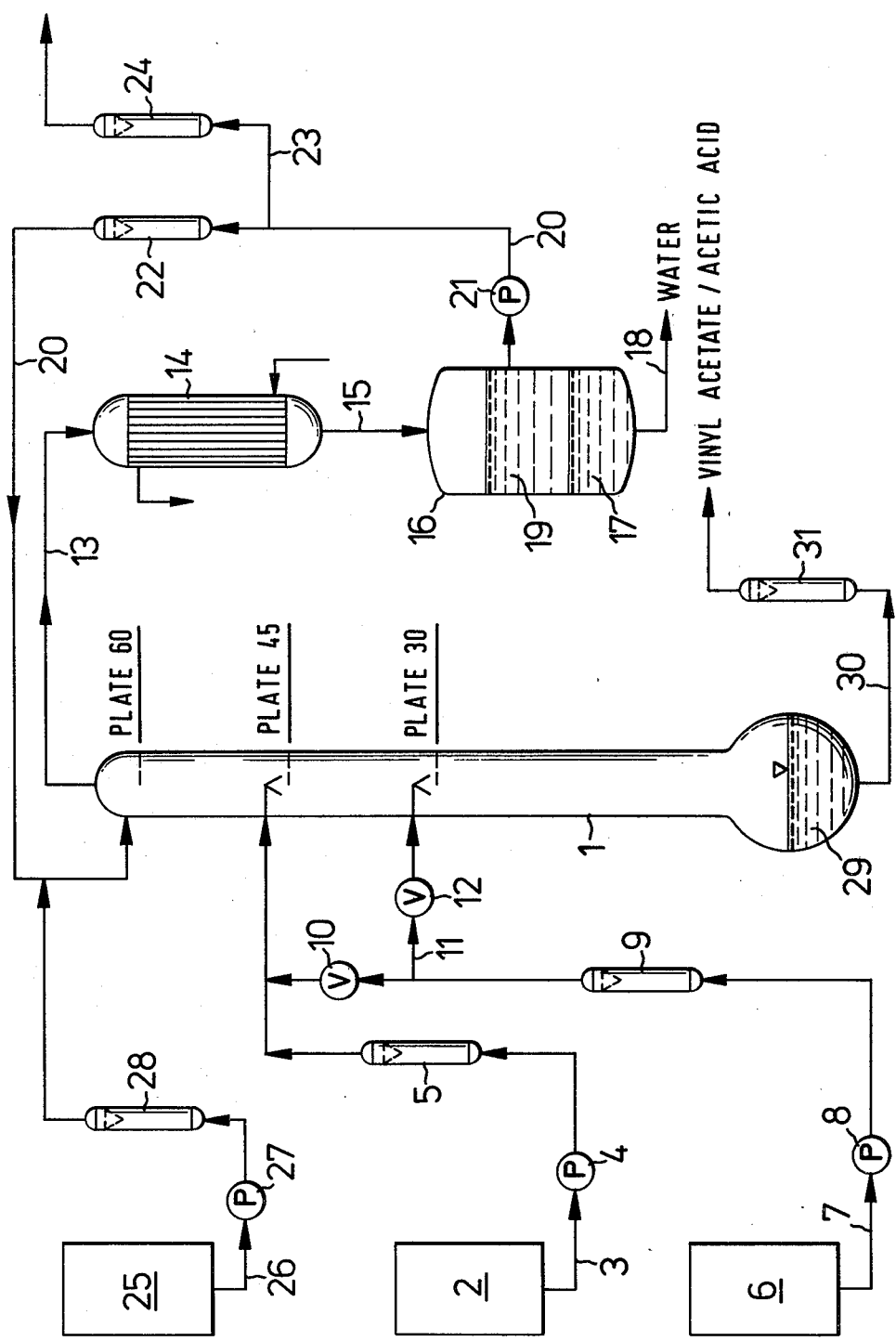

PROCESS FOR SEPARATING WATER FROM MIXTURES THEREOF WITH VINYL ACETATE AND ACETIC ACID

It is known to manufacture vinyl acetate by reaction of ethylene with acetic acid and oxygen or oxygen-containing gases in the gaseous phase in contact with solid bed catalysts. In general, the reaction is carried out under pressures of from 1 to 25 bar and at temperatures of from 100° to 250° C. Suitable catalysts contain a noble metal component and an activator component. The noble metal component consists of palladium and/or compounds thereof, it may additionally contain gold or compounds thereof. The activator component consists of compounds of elements of the first main group and/or the second main group of the periodic table and/or cadmium. The active components are finely distributed on the carrier material, which is, in general, silicic acid or aluminium oxide.

The catalyst usually has a palladium content of from 0.5 to 5% by weight.

If gold or a gold compound is used, it is added in an amount of from 0.01 to 4% by weight.

Each individual activator is normally added also in an amount of from 0.01 to 4% by weight. In each case the percentages indicate the metal portion of the respective component, calculated on the total amount of supported catalyst. The following catalysts are preferred: palladium/alkali metal/cadmium and palladium/gold/alkali metal. The finished catalyst may contain palladium and gold in metal form or as compounds. As alkali metal potassium is preferred (in the form of a carboxylate).

Especially preferred are palladium acetate/potassium acetate/cadmium acetate and palladium acetate/barium acetoaurate/potassium acetate catalysts.

As a result of stoichiometry one mol of water is formed for each mol of vinyl acetate:

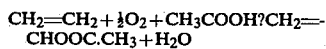

Owing to the fact that part of the reacted ethylene is oxidized to give $CO_2$ and water

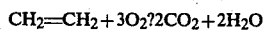

more than 1 mol of water is formed for each mol of vinyl acetate. In general, the weight of the water formed is approximately one fourth of the weight of the vinyl acetate produced.

The mixture used for the reaction contains a manifold molar excess of ethylene over the stoichiometric amount. Accordingly, the conversion of ethylene in the reaction is rather low and the unreacted ethylene has, therefore, to be recycled into the reaction. When the gas mixture has left the reactor, the vinyl acetate is separated therefrom in two or more stages. The hot reaction mixture leaving the reactor and consisting essentially of unreacted ethylene, unreacted acetic acid, unreacted oxygen, vinyl acetate, reaction water, $CO_2$ and inert substances introduced with oxygen and ethylene (for example $N_2$ and argon) is first cooled, whereby the main portion of acetic acid, vinyl acetate and water is condensed. In the following the liquid mixture obtained is named "condensate". According to the partial pressure part of the vinyl acetate (and of acetic acid and water) remains in the residual gas which has not been condensed and which mainly consists of ethylene, $CO_2$ and inert components. The latter vinyl acetate portion is removed from the residual gas prior to its recycling into the reaction in a wash tower operated with acetic acid as absorption liquid. The solution formed, named in the following also "run-off of sump of acetic acid wash" is combined according to the state of the art with the condensate to give the so-called "crude vinyl acetate." The condensate contains about 15 to 30% by weight of vinyl acetate and 6 to 11% by weight of water, the balance being acetic acid and traces of other by-products such as ethyl acetate, ethylene diacetate and acetaldehyde. The amount of condensate is equal to about 1 to 3 times the amount of the run-off of the sump of the acetic acid wash, which contains about 15 to 30% by weight of vinyl acetate and 1 to 3% by weight of water, that is to say contains less water than the condensate. The remainder of said run-off essentially consists of acetic acid. The crude vinyl acetate formed of the condensate and the run-off of the acetic acid wash contains about 15 to 30% by weight of vinyl acetate, 5 to 8% by weight of water, the remainder essentially being acetic acid. The crude vinyl acetate is separated by distillation into pure vinyl acetate and acetic acid which is recycled into the reaction.

The crude vinyl acetate is usually worked up by distillation according to two known processes. In one process (for example as disclosed in DE-OS Nos. 1,807,738 and DE-OS 1,768,412) vinyl acetate and water are distilled off at the head of a first column and acetic acid is discharged as sump product. The distillate separates into two phases of which the water phase is removed. Part of the vinyl acetate phase is used as reflux and simultaneously serves to form an azeotrope with the water to be distilled at the head. The remaining portion of the vinyl acetate phase (saturated with water) is dried in a second column by distilling off part thereof as azeotrope at the head together with the water still contained therein. The remainder passes into the anhydrous sump of the second column and is worked up in a third column to pure vinyl acetate which distills at the head and high boiling components and polymers which are discharged from the sump.

In the second process for working up crude vinyl acetate, as disclosed in DE-PS Nos. 1,282,014 and DE-PS 1,668,063, the water is distilled off in a first column using vinyl acetate for forming an azeotrope, the water phase is removed from the distillate separating into two phases and the total amount of the vinyl acetate phase is recycled into the column. According to a special embodiment of this process the column is provided with a head for the separation of low boiling components (for example acetaldehyde) having a boiling point below that of vinyl acetate. In this case vinyl acetate and water are discharged at a point below the head and transferred to a phase separator. The water phase is again discharged and the vinyl acetate phase is recycled into the column at a point below the discharge of vinyl acetate/water. The low boiling constituents can be removed directly at the top of the column head in this case. As sump product an anhydrous mixture of vinyl acetate/acetic acid is discharged which is separated in a second column into pure vinyl acetate (head product) and acetic acid (sump product).

In these two processes for working up the separation of the water requires 60 to 80% of the total energy necessary for the manufacture of pure vinyl acetate. Any improvement in the distillative water separation therefore constitutes a considerable improvement. The percentage of water in the distillate of the column for azeotropic dehydration is a measurement for the energy consumption. A high water concentration in the distillate means that a smaller amount of vinyl acetate has evaporated in the azeotropic dehydration and that, consequently, less energy has been consumed than in the case of a lower water concentration in the distillate.

It is the object of the present invention to provide a process wherein the energy consumption for the dehydration of the crude vinyl acetate is considerably diminished.

The process for separating water from the gas mixture, obtained in the manufacture of vinyl acetate by reacting ethylene with acetic acid and oxygen in the gaseous phase in contact with catalysts containing palladium or palladium compounds and consisting essentially of acetic acid, vinyl acetate, water, carbon dioxide and ethylene, wherein (a) the gas mixture leaving the reaction zone is condensed to give a condensate containing the main amount of acetic acid, of vinyl acetate and of water and (b) an acetic acid solution containing the residual amount of vinyl acetate and water is prepared by absorption of the non-condensed gas in acetic acid, comprises (c) introducing the condensate obtained in step (a) and the solution obtained in step (b) separately from each other into the same distillation column, the feeding point of the condensate being above the feeding point of the solution, distilling off the water at the head of said column as azeotrope together with the vinyl acetate and (d) removing the water phase from the distillate separating into a water phase and a vinyl acetate phase.

Pure vinyl acetate is then obtained from the vinyl acetate phase, for example in the manner described in one of the two aforesaid distillation processes.

In step (a) the gas mixture is usually cooled to 15° to 50° C., preferably 25° to 40° C. In step (b) the residual vinyl acetate and water are normally absorbed in a wash column in acetic acid as absorption agent. The distillation column used in step (c) usually has 50 to 80 trays and the feeding points for the condensate and the solution are normally separated from each other by 4 to 30 and preferably 6 to 20 trays. Generally, the feeding point of the condensate is at least 5 trays below the head of the column and at least 30 trays above the sump of the column.

By introducing the condensate of step (a) having a higher water content and the solution of step (b) having a lower water content at different points of the column a distillate is obtained which has a much higher water content than that of a process with common feeding according to the state of the art.

The following examples illustrate the invention. They are carried out in a unit as shown diagrammatically in the drawing.

GENERAL TEST CONDITIONS WITH REFERENCE TO THE DRAWING

A bubble tray column (1) made from glass and provided with vacuum jacket, electric sump heating, 60 trays, internal diameter 50 mm, is charged at the 45th tray with condensate (rich in water) from reservoir (2) through conduit (3) and via pump (4) and flow meter (5). Discharged run-off of sump (poor in water) of the acetic acid wash from reservoir (6) is introduced into column (1) via conduit (7), pump (8) and flow meter (9) either together with the condensate via valve (10) and conduit (3) (comparison) at the 45th tray or it is fed separately therefrom to the 30th tray (according to the invention) via conduit (11) and valve (12). The vapors issuing at the head of column (1) are passed through conduit (13) into water cooler (14) and the distillate liquefied in the cooler passes through conduit (15) into reservoir (16), in which it separates into two phases. The lower aqueous phase (17) is withdrawn through conduit (18) and rejected. The vinyl acetate phase (19) is discharged through conduit (20). It is recycled to the head of column (1), in the manner described in the aforesaid second process for vinyl acetate work-up, via pump (21) and flow meter (22)-after having removed a small part via conduit (23) and flow meter (24) for removing small amounts of acetaldehyde formed as a result of vinyl acetate hydrolysis. A stabilizer solution from reservoir (25) is introduced at the head of column (1) via conduit (26), pump (27), flow meter (28) and conduit (20). The liquid level in the sump (29) of column (1) is kept constant by discharging appropriate amounts of anhydrous vinyl acetate/acetic acid mixture via conduit (30) and flow meter (31).

COMPARATIVE EXAMPLE

The unit described above is used. Reservoir (2) contains a mixture of 30% by weight of vinyl acetate, 11% by weight of water, 59% by weight of acetic acid (condensate obtained by cooling the gas mixture leaving a vinyl acetate reactor). Reservoir (6) contains a mixture of 30% by weight of vinyl acetate, 2% by weight of water and 68% by weight of acetic acid (run-off of sump of acetic acid wash of the non condensed residual gas).

The 45th tray of column (1) is charged with 1,000 g/hr of the mixture of reservoir (2) and, with valve (10) being open and valve (12) being closed, with 600 g/hr of the mixture of reservoir (6), which corresponds to a total feed at the 45th tray of column (1) of 1,600 g/hr containing 30% by weight of vinyl acetate, 7.6% by weight of water and 62.4% by weight of acetic acid. The heating of the sump of column (1) is adjusted in such a manner that 2,400 g/hr of organic phase are collected in collecting vessel (16). The entire amount of organic phase (19) is recycled to the head of column (1) via pump (21) and flow meter (22). 20 g/hr are withdrawn from this reflux via flow meter (24).

A solution of 1% by weight of hydroquinone in vinyl acetate from reservoir (25) is pumped into the head of column (1) in an amount of 20 g/hr.

1,500 g/hr of vinyl acetate/acetic acid mixture containing 1.9% by weight of water are discharged from the sump of column (1).

In collecting vessel (16) 95 g/hr of aqueous phase (17) are obtained corresponding to 3.8% of the total distillate (aqueous plus organic phase).

EXAMPLE

The process is carried out as described in the comparative example with the exception that the two mixtures are introduced at different points of column (1). The mixture from reservoir (2) is fed at the 45th tray of column (1) as in the comparative example whereas the mixture from reservoir (6) is fed, with valve 10 being closed and valve (12) being open, to the 30th tray of column (1). 1,480 g/hr of vinyl acetate/acetic acid mixture having a water content of 0.3% by weight are discharged from the sump of column (1).

In collecting vessel (16) 2,400 g/hr of organic phase (19) and 120 g/hr of aqueous phase (17), in other words 4.8% by weight of the total distillate, are aqueous phase.

As compared with the comparative example, the water concentration (i.e. the proportion by weight of aqueous phase) in the distillate has been increased from 3.8% by weight to 4.8% by weight, which corresponds to a relative increase of about 25%.

This means a saving of distillation energy, calculated on the total distillation (evaporation energy for organic phase and aqueous phase), of about 20% over the comparative example.

What is claimed is:

1. In a method for the manufacture of vinyl acetate by gaseous phase reaction of ethylene with acetic acid and oxygen in the presence of a catalyst containing palladium, or compounds thereof, to form a gaseous mixture of acetic acid, vinyl acetate, water, carbon dioxide and ethylene as main components wherein said gaseous mixture is condensed to form a condensate containing the major amount of acetic acid, vinyl acetate and water present in said gaseous mixture and absorbing the residual amount of vinyl acetate and water in said gaseous mixture in acetic acid to form an acetic acid solution, the method which comprises feeding separately the condensate and the acetic acid solution to a separation column containing 50 to 80 trays said condensate being fed thereto at a point located 4 to 30 trays above that point at which said acetic acid solution is fed to said column, forming a distillate of water in the overhead stream as an azeotrope with vinyl acetate which distillate forms a water and a vinyl acetate phase and removing the water phase therefrom.

2. The method of claim 1 wherein the condensate is fed to said column at a point located 6 to 20 trays above that point at which said acetic acid solution is fed to said column.

* * * * *

UNITED STATES PATENT AND TRADEMARK OFFICE
CERTIFICATE OF CORRECTION

PATENT NO. : 4,353,783
DATED : October 12, 1982
INVENTOR(S) : Roscher et al.

It is certified that error appears in the above-identified patent and that said Letters Patent are hereby corrected as shown below:

On the title page, Item [73], after "Germany," there should be added --and Wacker-Chemie GmbH, Munich, Fed. Rep. of Germany--.

Signed and Sealed this

Twelfth Day of April 1983

[SEAL]

Attest:

GERALD J. MOSSINGHOFF

Attesting Officer  Commissioner of Patents and Trademarks